(12) United States Patent
Anderson

(10) Patent No.: US 10,441,467 B1
(45) Date of Patent: Oct. 15, 2019

(54) HIGH PERFORMANCE GOGGLE WITH WIDE FIELD OF VIEW

(71) Applicant: William B. Anderson, Carlsbad, CA (US)

(72) Inventor: William B. Anderson, Carlsbad, CA (US)

( * ) Notice: Subject to any disclaimer, the term of this patent is extended or adjusted under 35 U.S.C. 154(b) by 265 days.

(21) Appl. No.: 15/370,909

(22) Filed: Dec. 6, 2016

Related U.S. Application Data

(60) Provisional application No. 62/264,296, filed on Dec. 7, 2015.

(51) Int. Cl.
*A61F 9/02* (2006.01)

(52) U.S. Cl.
CPC .............. *A61F 9/025* (2013.01); *A61F 9/027* (2013.01)

(58) Field of Classification Search
CPC ................................. A61F 9/025; A61F 9/027
See application file for complete search history.

(56) References Cited

U.S. PATENT DOCUMENTS

| | | | | | |
|---|---|---|---|---|---|
| 5,138,723 | A | * | 8/1992 | Bolle | A61F 9/02 2/430 |
| 6,076,196 | A | * | 6/2000 | Masumoto | A61F 9/028 2/425 |
| 6,292,983 | B1 | * | 9/2001 | Giaquinta | A44B 11/006 24/163 R |
| 2003/0221246 | A1 | * | 12/2003 | Schary | A61F 9/027 2/453 |
| 2007/0279578 | A1 | * | 12/2007 | Stanley | A61F 9/025 351/62 |
| 2008/0034480 | A1 | * | 2/2008 | Chen | A61F 9/025 2/426 |

* cited by examiner

*Primary Examiner* — Anna K Kinsaul

(57) ABSTRACT

Embodiments are directed to a high performance safety goggle that permits a wide field of view for the user.

19 Claims, 11 Drawing Sheets

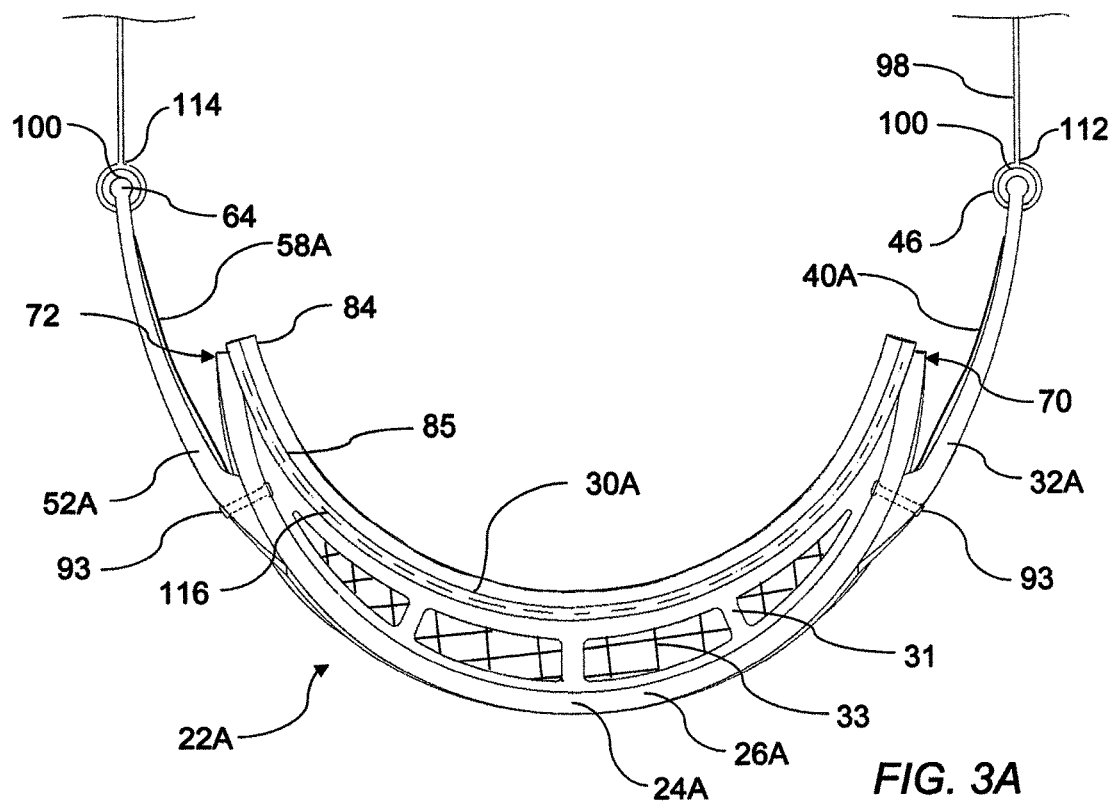
FIG. 3A

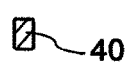 

HIGH PERFORMANCE GOGGLE WITH WIDE FIELD OF VIEW

RELATED APPLICATIONS

This application claims priority under 35 U.S.C. 119(e) from U.S. Provisional Patent Application Ser. No. 62/264,296, filed Dec. 7, 2015, by William B Anderson, titled High Performance Goggle with Wide Field of View, which is hereby incorporated by reference herein in its entirety.

BACKGROUND

Outdoor activities that involve high speeds, cold conditions, dusty conditions etc. often require or invite the use of eye protection, such as a goggle in order to protect the participant's eyes. Goggle models are available today from a host of manufacturers and include a wide variety of sizes, shapes, colors, designs and features. There seems to be a goggle available for any given application or user taste. Many different types of goggle are available for outdoor sports such as snowboarding, skiing, bobsledding, motorcycle riding, snowmobiling, mountain biking as well as others. Many of these endeavors involve high speeds and also admit to the use of a crash helmet to protect the participant's head from injury in the event of a fall during the activity. Although most of the crash helmets marketed for these activities have a wide opening that does not hinder the participant's field of view, particularly the peripheral field of view, many of the currently available goggles that may be used alone or in conjunction with the use of a crash helmet do in fact hinder the participant's peripheral vision. Some googles currently on the market have a large negative impact on a user's peripheral vision, particularly in the lateral peripheral orientation. Because the activities that require the use of a protective goggle often involve high speeds, dangerous obstacles, and/or participation in close proximity to other participants, this reduction of peripheral vision may a serious negative affect on the safety of the goggle wearer. Specifically, it is often very useful for a goggle wearer to know what is going on around and behind them as well as what is coming up in front of them. What has been needed is a goggle that provides the requisite protection to the user's eyes but without significantly hindering the user's peripheral vision.

SUMMARY

Some embodiments of a goggle assembly include a goggle frame having an anterior frame portion with a lens receptacle disposed about an interior perimeter that defines a lens aperture. The goggle frame also includes a posterior frame portion which is disposed adjacent and secured to the anterior frame portion and which is configured to fit to an outside surface of a wearer's face around the wearer's eyes. The goggle assembly further includes an elongate left upper extension having a goggle end secured to an upper portion of the anterior frame portion, a strap end that is disposed opposite the goggle end and a length sufficient to allow the left upper extension to wrap behind a left side of the goggle frame such that the strap end is disposed completely outside a wearer's left side field of peripheral vision. An elongate left lower extension includes a goggle end which is secured to a lower portion of the anterior frame portion, a strap end that is disposed opposite the goggle end and a length sufficient to allow the left lower extension to wrap behind a left side of the goggle frame such that the strap end is disposed completely outside a wearer's left side field of peripheral vision. A left strap post has an upper end which is secured to the strap end of the left upper extension and a lower end which is secured to the strap end of the left lower extension. An elongate right upper extension includes a goggle end which is secured to an upper portion of the anterior frame portion, a strap end that is disposed opposite the goggle end and a length that is sufficient to allow the right upper extension to wrap behind a right side of the goggle frame such that the strap end is disposed completely outside a wearer's right side field of peripheral vision. An elongate right lower extension includes a goggle end which is secured to a lower portion of the anterior frame portion, a strap end that is disposed opposite the goggle end and which includes a length that is sufficient to allow the right lower extension to wrap behind a right side of the goggle frame such that the strap end is disposed completely outside a wearer's right side field of peripheral vision. A right strap post has an upper end secured to the strap end of the right upper extension and a lower end secured to the strap end of the right lower extension.

Certain embodiments are described further in the following description, examples, claims and drawings. These features of embodiments will become more apparent from the following detailed description when taken in conjunction with the accompanying exemplary drawings.

BRIEF DESCRIPTION OF THE DRAWINGS

FIG. 3A is a top view of a goggle assembly embodiment having extensions that are secured to the goggle frame by fasteners.

The drawings illustrate embodiments of the technology and are not limiting. For clarity and ease of illustration, the drawings may not be made to scale and, in some instances, various aspects may be shown exaggerated or enlarged to facilitate an understanding of particular embodiments.

DETAILED DESCRIPTION

Figure 1:
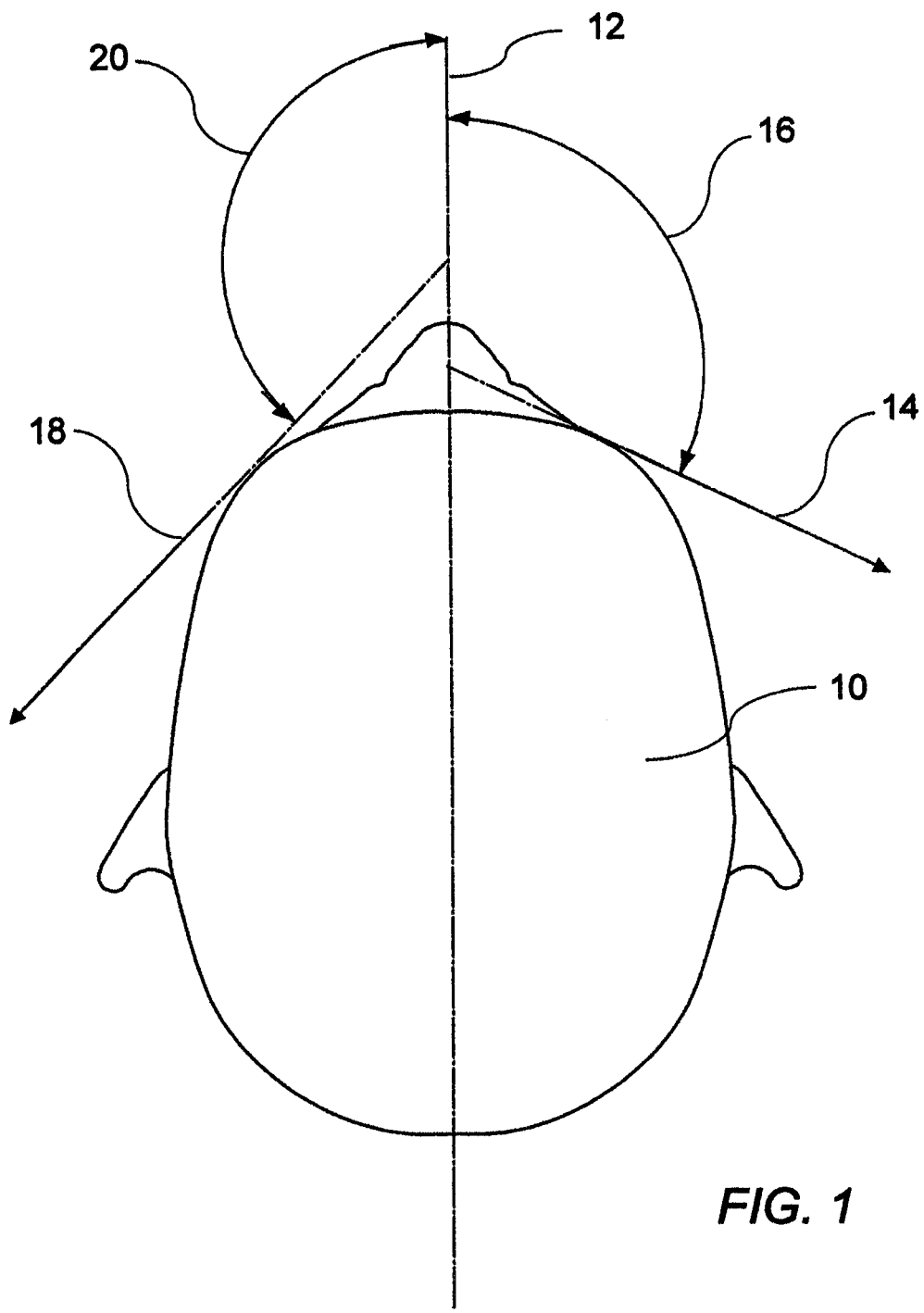
FIG. 1 is a schematic top view of an embodiment of a wearer's head.

As discussed above, there may be many advantages to the use of a goggle assembly that provides the wearer with a minimally restricted peripheral field of view. The full range of human peripheral vision is often underestimated by users of optical safety equipment, and, as such, the consumer may be unaware of just how much restriction of peripheral vision is caused by optical safety equipment such as a safety goggle. FIG. 1 shows a top view of an embodiment of a wearer's head 10 with a dashed line 12 indicating a lateral axis of symmetry of the wearer's head. An arrow 14 shows an approximation of the lateral angular limit of normal peripheral human vision with the person's head in a fixed position with eyes in a static position looking straight forward. Arrow 14 forms an angle 16 of about 110 degrees with respect to the axis of symmetry 12 on one side. As such, a typical person looking straight ahead with head and eyes fixed has an angular range of peripheral vision that may extend to a full angle of both sides of a person's vision of up to about 220 degrees. It has also been shown that the human eye may typically have an angular displacement of up to about 20 degrees relative to the lateral axis of symmetry 12 during a saccade wherein the person briefly glances to the side without turning their head to any significant degree. As such, a person's angular field of peripheral vision that includes saccade type eye movement or glances to each side of a person's vision may be a full angle including both sides of the person's view of up to about 260 degrees. Arrow 18 forms an angle 20 which may be up to about 130 degrees with respect to the axis symmetry 12 and represents an approximate angular limitation of a typical person's field of peripheral vision including saccades eye movement for one side.

As can be seen from FIG. 1, a normal person's angular field of peripheral vision extends far beyond a forward looking orientation or even a full 180 degree side to side view. In fact, a person can see objects disposed well behind them with their peripheral vision while their head is still facing straight forward. As such, safety eyewear such as a goggle that significantly impedes this full range of angular peripheral vision may be detrimental to the wearer's ability to see other participants nearby, obstacles or other objects of interest and may therefore affect the safety and/or performance of the wearer. Such a reduced field of vision may also give the wearer a sense of tunnel vision or a mild claustrophobic sensation. Many typical safety goggles currently available, particularly goggles used in conjunction with activities that include the use of a helmet, such as bicycle and motorcycle sports, allow for an angular field of peripheral vision of less than 180 degrees. As such, these currently available goggles significantly impede a user's field of view. Although the manufacturers of such currently available goggles claim to provide a broad field of view, the structure at the sides of the goggles, and particularly the structure of the elastic strap and strap attachment mechanism as well as portions of the anterior lens frame portion are disposed in the wearer's field of peripheral vision as described above.

Embodiments of a goggle assembly 22 that provide the wearer with a broad peripheral field of view are shown in FIGS. 2-11. The embodiments of the goggle assembly 22 include a goggle frame 24 that has an anterior frame portion 26 with a lens receptacle 28 disposed about an interior perimeter of the anterior frame portion 26 that defines a lens aperture 29. The goggle frame 24 also includes a posterior frame portion 30 which is disposed adjacent and secured to the anterior frame portion 26 and which is configured to fit to an outside surface of a wearer's face around the wearer's eyes. In some cases, the anterior frame portion 26 may be connected to the posterior frame portion 30 by webs 31 disposed therebetween. Openings disposed between such webs 31 may be covered with optional filter material 33 that may include a thin layer of porous mesh, foam or the like that allows air to pass therethrough but prevents dirt, dust, snow or the like to enter an interior volume of the goggle assembly 22.

The goggle assembly 22 further includes an elongate left upper extension 32 having a goggle end 34 secured to an upper portion 36 of the anterior frame portion 26, a strap end 38 that is disposed opposite the goggle end 34 and a length sufficient to allow the left upper extension 32 to wrap behind a left side of the goggle frame 24 such that the strap end 38 is disposed completely outside a wearer's left side field of peripheral vision. An elongate left lower extension 40 includes a goggle end 42 which is secured to a lower portion 43 of the anterior frame portion 26, a strap end 44 that is disposed opposite the goggle end 42 and a length sufficient to allow the left lower extension 40 to wrap behind a left side of the goggle frame 24 such that the strap end 44 is disposed completely outside a wearer's left side field of peripheral vision. A left strap post 46 has an upper end 48 which is secured to the strap end 38 of the left upper extension 32 and a lower end 50 which is secured to the strap end 44 of the left lower extension 40. The left strap post 46 may also be disposed completely outside of the wearer's left side field of peripheral vision. A gap 51 indicated by arrow 53 in FIG. 4 indicates a rearward spatial separation between a left edge of the lens aperture 29 and a front edge of the left strap post 46. The gap 51 may be chosen on each side of the goggle assembly 22 to keep the strap posts 46, 64 completely outside of the wearer's static and saccade augmented field of peripheral vision. In some cases, the gap 51 may be up to about 5 inches, more specifically, about 0.2 inches to about 3 inches, and even more specifically, about 0.5 inches to about 1.5 inches.

An elongate right upper extension 52 includes a goggle end 54 which is secured to an upper portion 36 of the anterior frame portion 26, a strap end 56 that is disposed opposite the goggle end 54 and a length that is sufficient to allow the right upper extension 52 to wrap behind a right side of the goggle frame 24 such that the strap end 56 is disposed completely outside a wearer's right side field of peripheral vision. An elongate right lower extension 58 includes a goggle end 60 which is secured to a lower portion 43 of the anterior frame portion 26, a strap end 62 that is disposed opposite the goggle end 60 and which includes a length that is sufficient to allow the right lower extension 58 to wrap behind a right side of the goggle frame 24 such that the strap end 62 is disposed completely outside a wearer's right side field of peripheral vision. A right strap post 64 has an upper end 66 secured to the strap end 56 of the right upper extension 52 and a lower end 68 secured to the strap end 62 of the right lower extension 58. The right strap post 64 may also be disposed completely outside of the wearer's right side field of peripheral vision.

Figure 2:
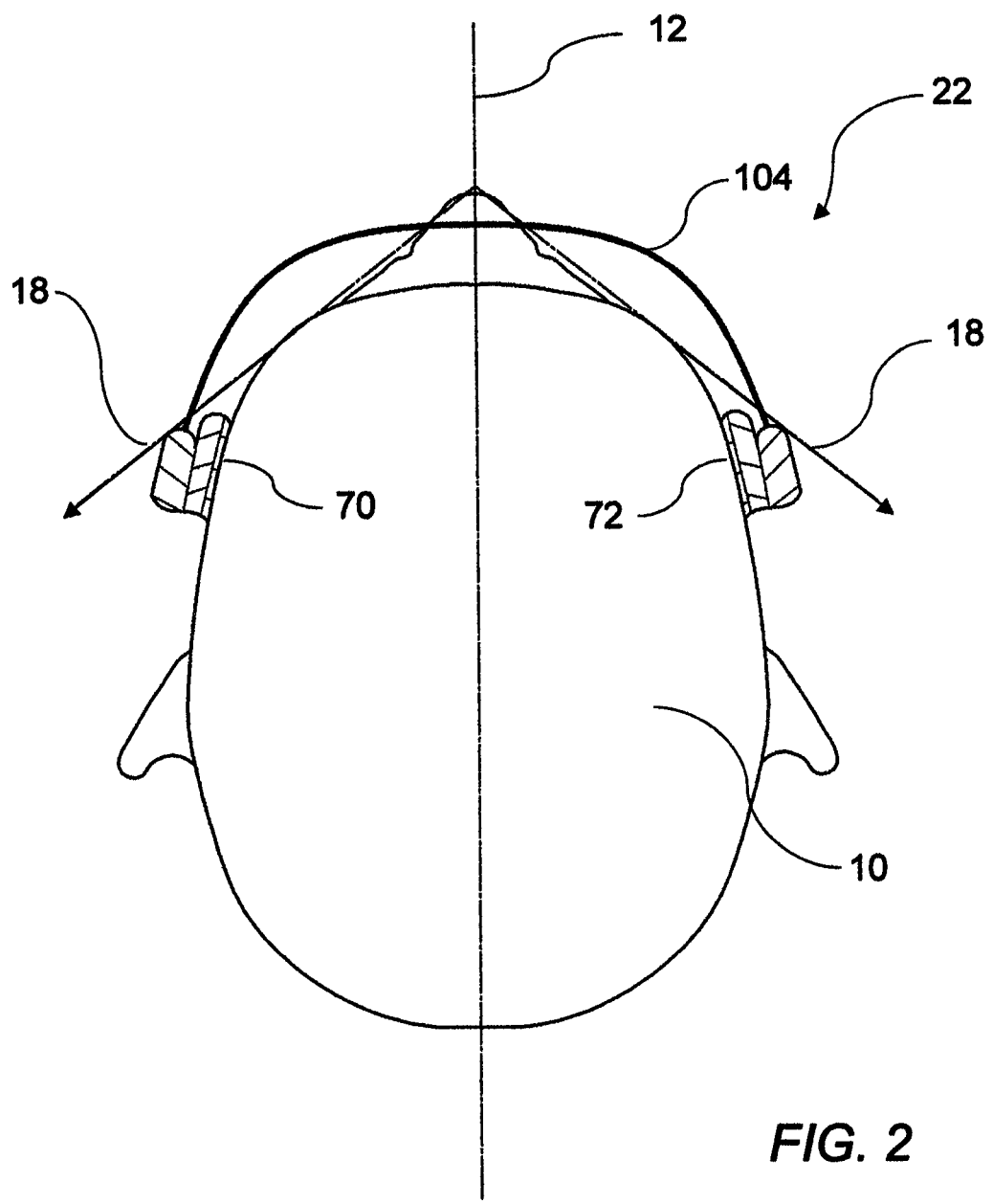
FIG. 2 is a schematic top view of the embodiment of the wearer's head of FIG. 1 showing maximum peripheral vision including saccades movement unobstructed by a left side length of the goggle frame and a right side length of the goggle frame.
Figure 3:
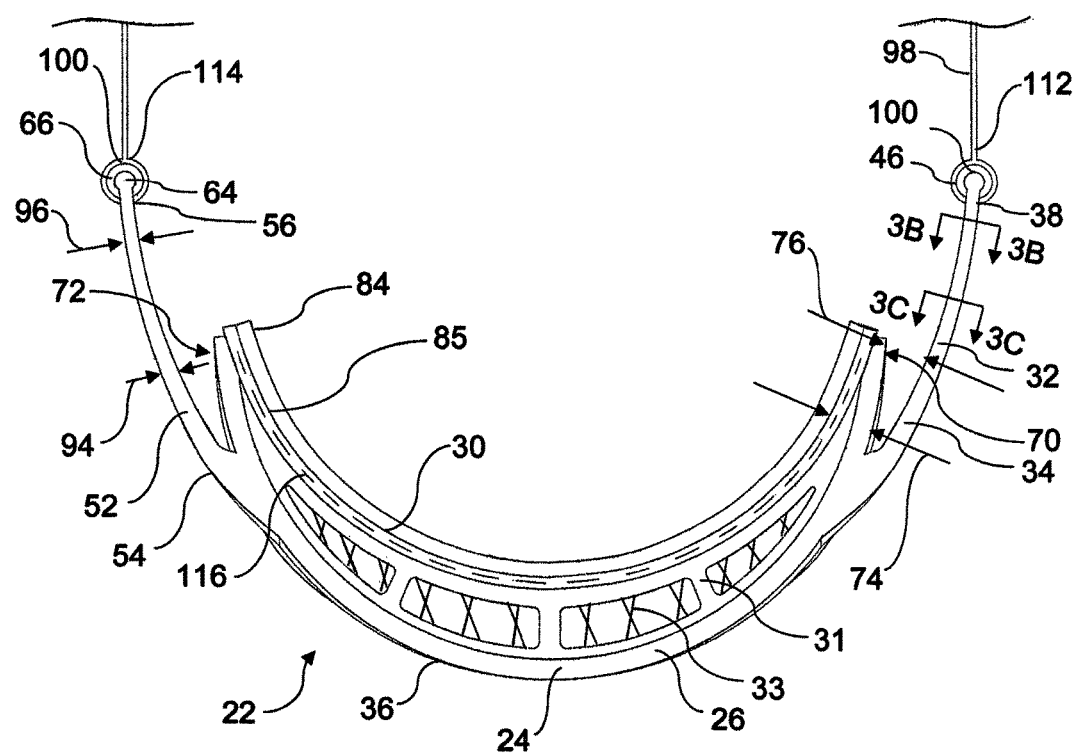
FIG. 3 is a top view of a goggle assembly embodiment.

In some cases, as shown in FIG. 2, a left side portion 70 of the goggle frame 24 and a right side portion 72 of the goggle frame 24 may be shaped to permit a substantially full peripheral field of view through the lens aperture 29 of the wearer including full static angular peripheral vision and peripheral vision during saccades movement of the wearer's eye as shown in FIG. 1. For some embodiments, a separation between outside surfaces of the outer ends of the posterior frame portion 30 and anterior frame portion 26 decreases towards the outer ends of the goggle frame 24 as shown in FIG. 3. FIG. 3 shows a first pair of opposed arrows 74 that indicate a separation between an outer surface of the anterior frame portion 26 and an outside surface of the posterior frame portion 30 which is greater than a separation of these outside surfaces indicated by a second pair of arrows 76 which are disposed at the outer ends of the frame portions 26, 30. That is, the separation between the anterior frame portion 26 and posterior frame portion 30 tapers to a reduced separation towards the outer ends 70, 72 of the goggle frame 24. In some cases, the separation between the anterior frame portion 26 and posterior frame portion 30 is tapered such that there is no separation between the anterior frame portion 26 and posterior frame portion 30 at the outer ends 70, 72 of the goggle frame 24 and the frame portions 26 and 30 may actually merge together at the outer ends 70, 72 of the goggle frame 24 in some cases.

Figure 9:
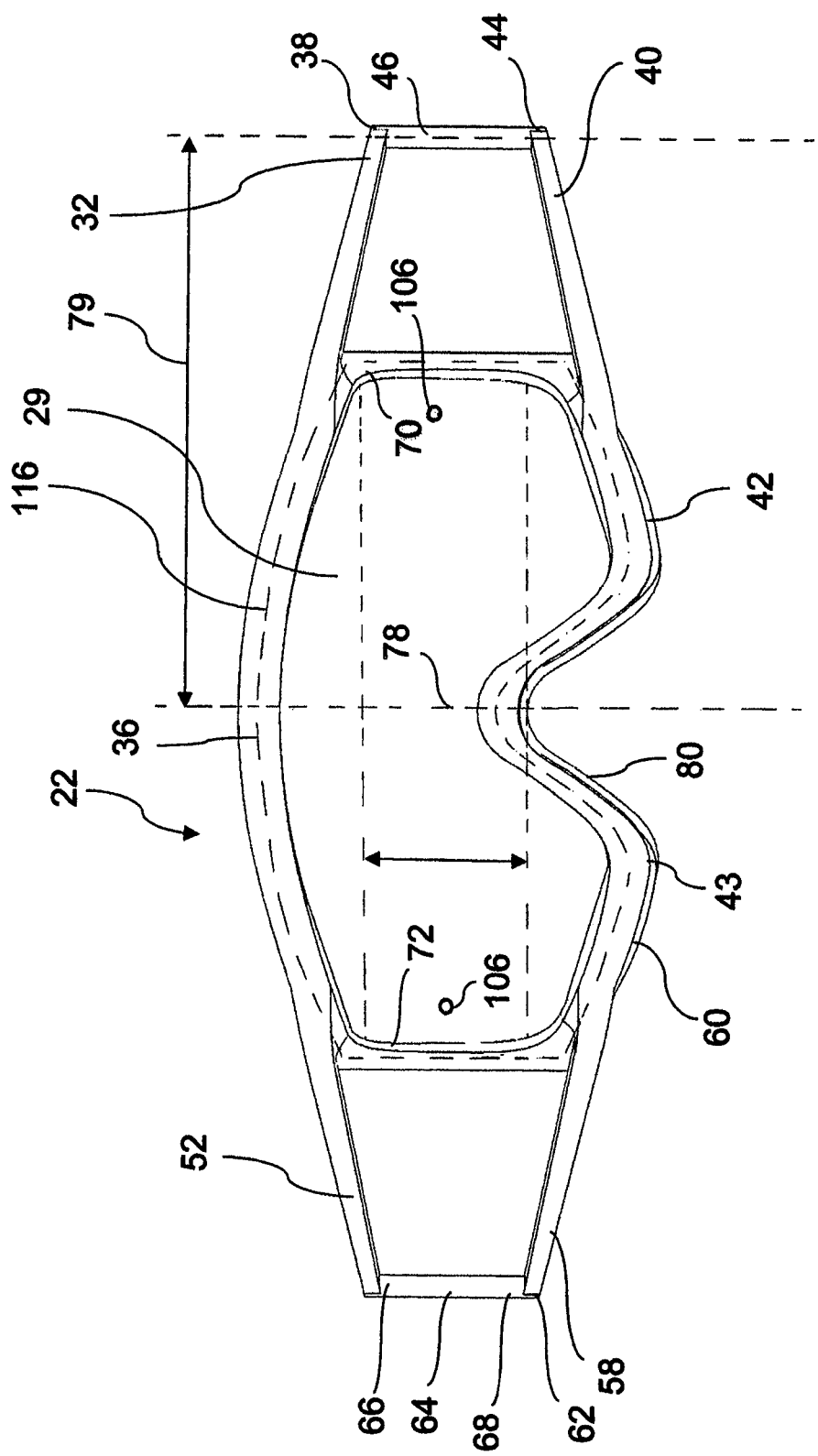
FIG. 9 is front view of the goggle assembly embodiment of FIG. 3.
Figure 10:
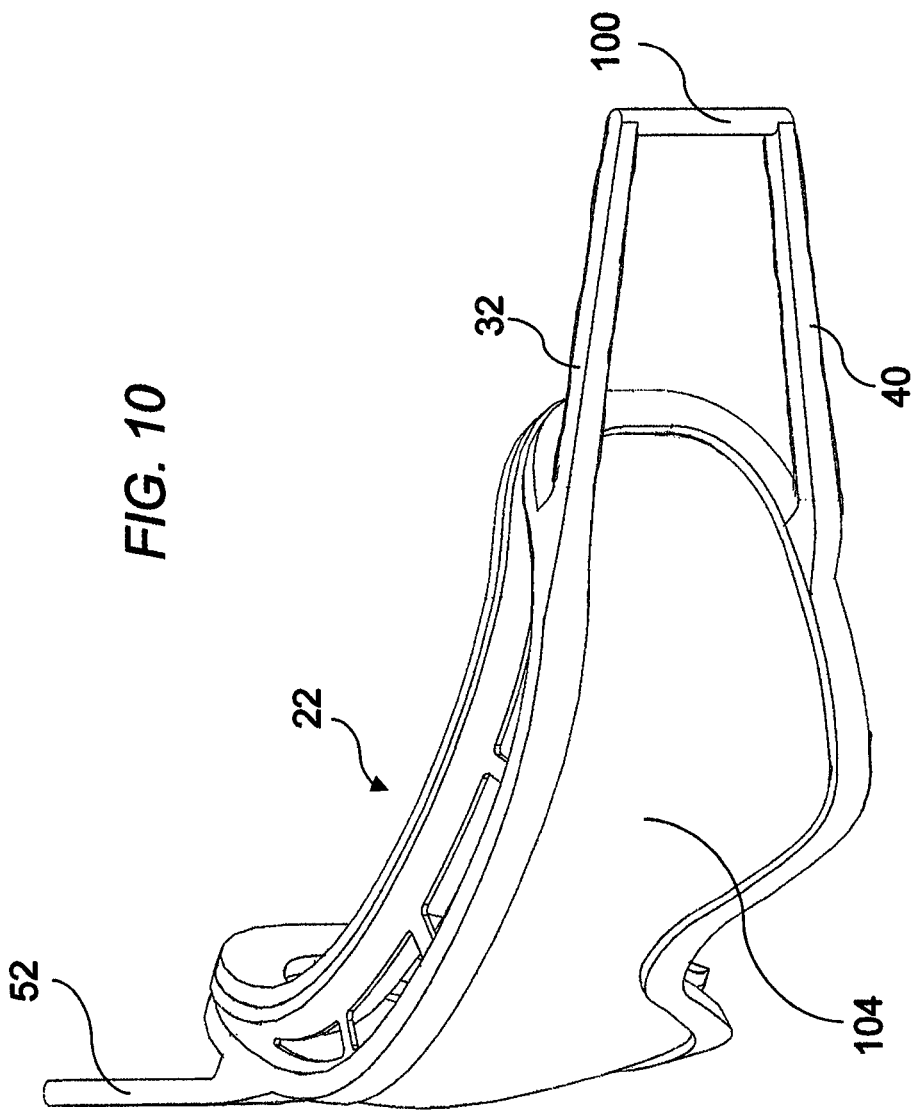
FIG. 10 is a perspective view of the goggle assembly embodiment of FIG. 4.
Figure 11:
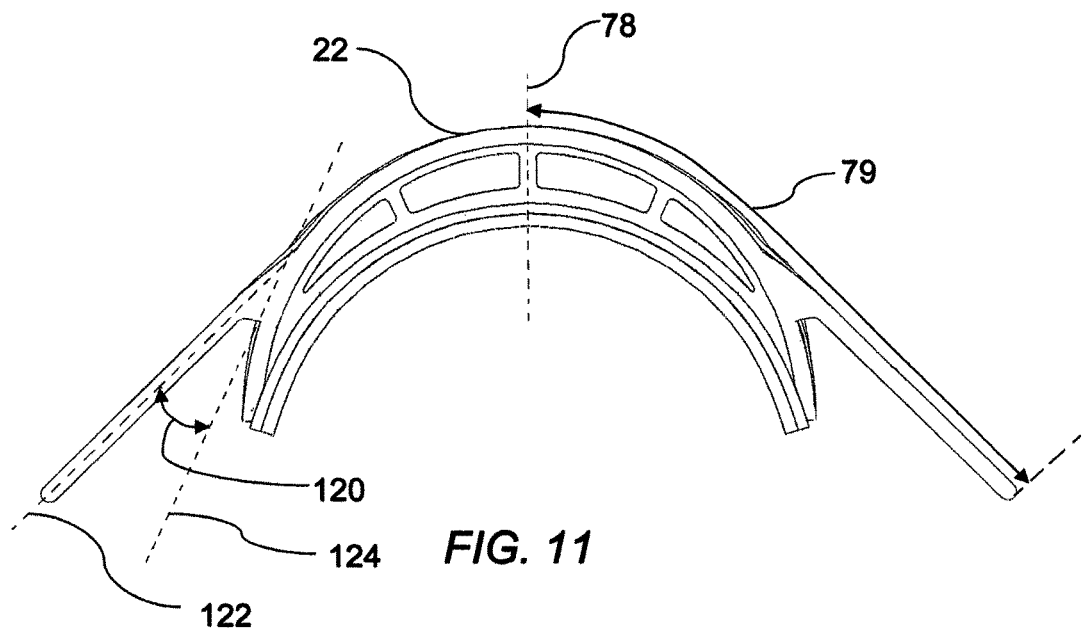
FIGS. 11 and 12 are top views of the goggle assembly embodiment of FIG. 4 with the extensions in a straightened and inwardly curved configuration respectively.
Figure 12:
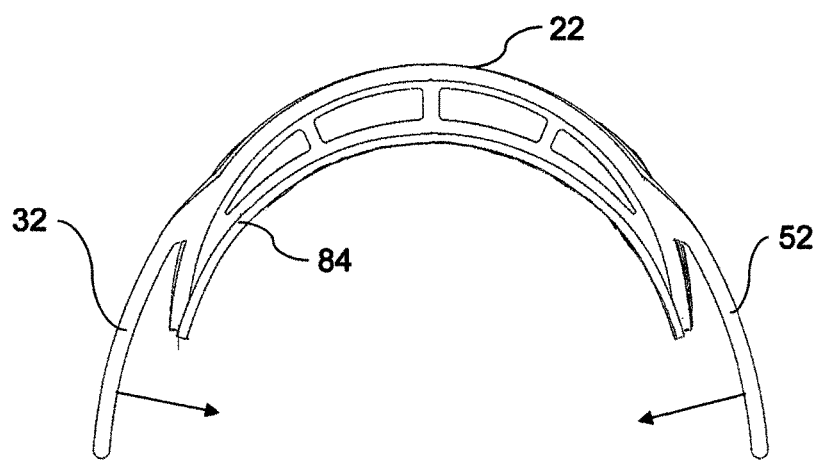

For some embodiments, the left side portion 70 of the goggle frame 24 and the right side portion 72 of the goggle frame 24 may each be shaped and configured so as to provide a lateral peripheral angle of vision that extends to at least about 125 degrees from a lateral axis of symmetry line 12 of a wearer's head 10. In some cases, the left upper extension 32, the left lower extension 40, the right upper extension 52, and right lower extension 58 may include a length measured from a horizontal center 78 of the goggle frame 24 which is sufficient to allow the extension to wrap around respective peripheral edges of cut outs of a helmet completely outside the wearer's field of peripheral vision. Although a gap 51 of up to 5 inches is discussed herein, it should be noted that in many cases it may be desirable to minimize the gap 51 while still maintaining the position of the strap posts 46, 64 outside of the wearer's field of dynamic peripheral vision that includes saccades eye motion. This is because as the length of the extensions 32, 40, 52 and 58 increases, so does the tendency of these extensions 32, 40, 52 and 58 to get tangled when the goggle assembly 22 is being removed from a helmet after use or during storage. As such, for some embodiments, it may be desirable for the post end of each extension 32, 40, 52 and 58 to extend from the horizontal center line 78 of the goggle assembly 22 along the adjacent respective frame sections only so far as necessary to extend out of the wearer's dynamic field of vision or any other desired expanded field of vision suitable for such a goggle assembly which may be less than a full dynamic field of view in some instances. For some embodiments, the post end of each extension 32, 40, 52 and 58 may extend a distance of about 6 inches to about 10 inches, more specifically, about 6.5 inches to about 8.5 inches from the centerline 78 of the goggle assembly 22 as shown in FIGS. 9 and 11 and indicated by arrow 79.

For some embodiments, the goggle frame 24 may be configured to provide an unobstructed view through the lens aperture 29 at a peripheral view angle with respect to an axis of symmetry 12 of a wearer's head 10 on each side of up to about 100 degrees, up to about 105 degrees, up to about 110 degrees, up to about 115 degrees, up to about 120 degrees, up to about 125 degrees or up to about 130 degrees. For some embodiments, the goggle frame 24 may include a nose cut out 80 disposed at the center of the lower portion 43 of the anterior frame portion 26 and a lower portion 82 of the posterior frame portion 30. In some instances, the goggle frame 24 may be made from a material including urethane, PVC, silicone or the like.

Referring to FIG. 3, an elastic foam gasket 84, as is commonly used for goggles, may be disposed on and secured to a face surface 85 the posterior frame portion 30. The foam gasket 84 may extend around the entire perimeter of the face surface of the posterior frame portion 30 and serve as an interface between the face surface 85 and a wearer's skin. The foam gasket 84 may be configured to provide a soft absorbent interface that conforms to the wearer's skin and provides a comfortable resilient fit.

Figure 4:
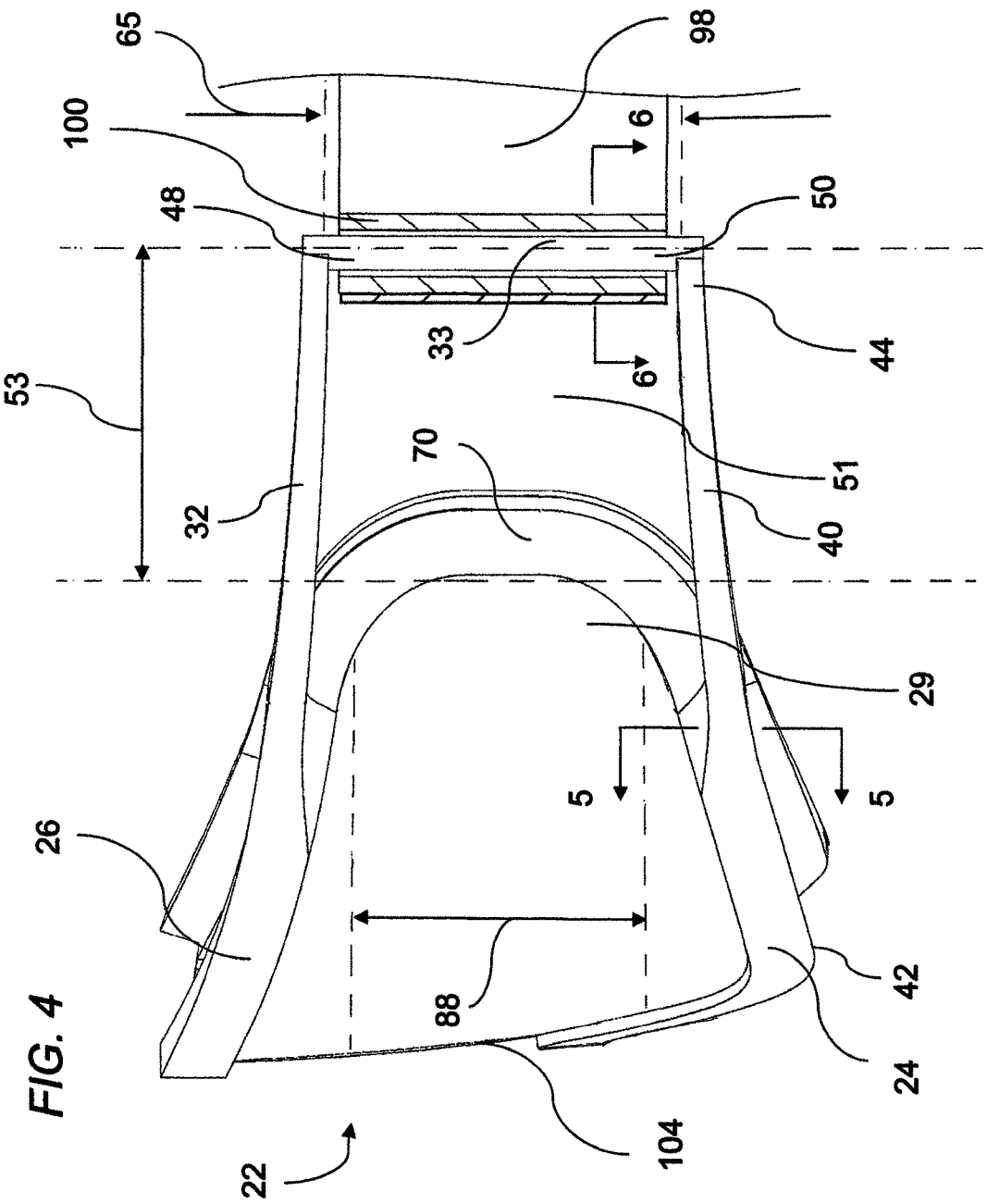
FIG. 4 is a side view of the goggle assembly embodiment of FIG. 3.
Figure 7:
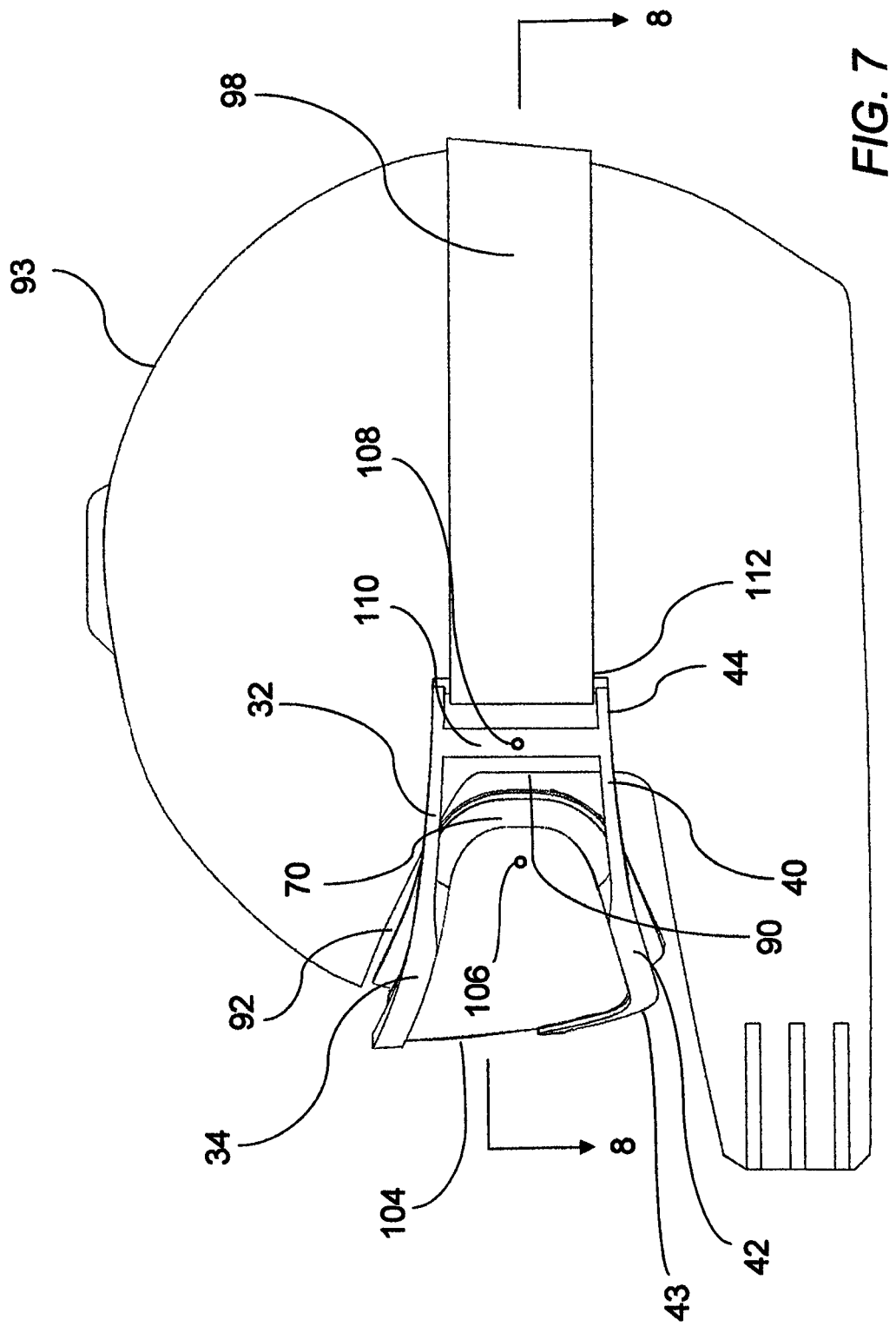
FIG. 7 is a side view of the goggle assembly embodiment of FIG. 3 disposed in a cut out of a helmet embodiment with an elastic strap of the goggle assembly wrapped around a back of the helmet.

In some cases, as shown in FIG. 7, the length of the strap posts 46, 64 and length of the elongate extensions 32, 40, 52, 58 being selected such that the strap posts 46, 64 are disposed in a substantially vertical orientation during use. The length of the strap posts 46, 64 (as indicated by arrow 65 of FIG. 4) and length of the elongate extensions 32, 40, 52, 58 may further be selected such that the upper extensions 32, 52 extend along the respective upper portion 36 of the anterior frame portion 26 and the lower extensions 40, 58 extend along the lower portion 43 of the anterior frame portion 26 in order to minimize impact on the wearer's field of view as shown in FIGS. 4 and 7. Such a configuration may also provide a band of unobstructed vision 86 having a vertical width, as indicated by arrow 88 in FIGS. 4 and 9, of at least about 1 inch, more specifically, at least about 1.5 inches.

Figure 8:
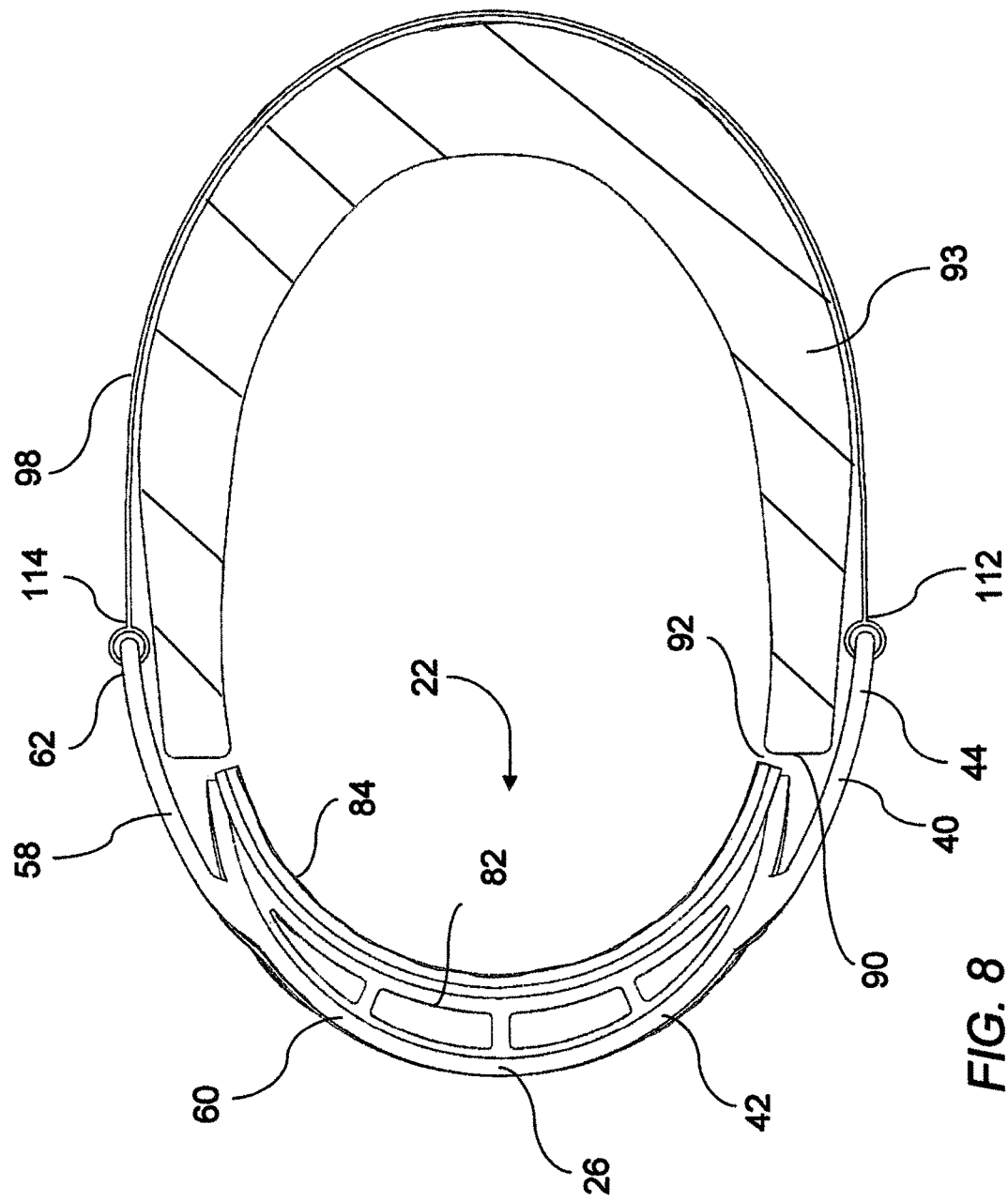
FIG. 8 is a transverse section view of the goggle assembly and helmet embodiment of FIG. 7 taken along lines 8-8 of FIG. 7.

In some instances the elongate extensions 32, 40, 52, 58 may include a flexible resilient structure configured to retain its shape in a relaxed unconstrained state but with sufficient flexibility to wrap around a wearer's head 10 and/or an edge of a helmet cut out 92 of a helmet 93 as shown in FIGS. 7 and 8. In some instances, the elongate extensions 32, 40, 52, 58 may be molded in monolithic structures as continuous extensions of the anterior frame portion 26 of the goggle frame 24 as shown in FIG. 3. In other instances, the elongate extensions 32, 40, 52, 58 may be formed as separate structures which are formed separately from the goggle frame 24A and then secured to the anterior frame portion 26A of the goggle frame 24A as shown in FIG. 3A. The elongate extensions 32A, 40A, 52A, 58A may be secured to the anterior frame portion 26A by fasteners such as rivets 93 shown in FIG. 3A disposed through the goggle ends of the elongate extensions 32, 40, 52, 58 and respective portions of the goggle frame 24. The elongate extensions 32A, 40A, 52A, 58A may also be secured to the goggle frame 24A by adhesive bonding, welding, mechanical capture/coupling or the like.

Figure 3B:
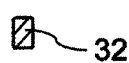
FIG. 3B is a transverse cross section view of the left upper extension and left lower extension taken along lines 3B-3B of FIG. 3.
Figure 3C:
FIG. 3C is a transverse cross section view of the left upper extension and left lower extension taken along lines 3C-3C of FIG. 3.

For some embodiments, the elongate extensions 32, 40, 52, 58 may include a tapered structure that tapers to a smaller transverse cross section from the goggle end to the strap end as shown in FIGS. 3, 3B and 3C. FIG. 3 shows a first pair of arrows 94 indicating a separation of opposed outside surfaces of the right upper elongate extension 52 which is greater than a separation of opposed outside surfaces of the elongate extension at a second pair of arrows 96 which are disposed near a strap end 56 of the right upper elongate extension 52. In some cases, the elongate extensions 32, 40, 52, 58 may include an inclusive taper angle of about 0.5 degrees to about 2 degrees, more specifically, about 0.5 degrees to about 1 degree, with a corresponding change in cross section area for each of the elongate extensions. In some cases, the elongate extensions 32, 40, 52, 58 may include materials such as polyurethane, polyvinylchloride (PVC), silicone or the like.

The right and left strap posts 46, 64 may serve as attachment interface between the elongate extensions 32, 40, 52, 58 of the goggle frame 24 and an elastic strap 98 that may be used to resiliently hold the goggle 22 against a wearer's face. In some cases, the right and left strap posts 46, 64 may be configured as rigid strap posts which are secured to respective strap ends of the extensions 32, 40, 52 and 58 by adhesive bonding, over-molding or the like. For some embodiments, rigid strap posts which are secured to the respective strap ends of the extensions may be made from rigid, high strength, lightweight materials such as fiber reinforced composites such as carbon fiber composites, fiberglass, metals such as aluminum and the like. In some instances, each strap post 46, 64 may include a tubular rigid outer sleeve 100 that extends from respective upper and lower ends of each strap post 46, 64. In some instances, each rigid outer sleeve 100 may include a split sleeve with an elongate tubular structure with a narrow longitudinal gap 102 in a wall of the tubular structure extending an entire longitudinal length of the rigid outer sleeve 100. Such rigid split sleeves 100 may have an inner lumen extending a length thereof and having a transverse diameter that closely matches an outer transverse diameter of strap post portions 46, 64. Such split sleeves 100 may be positioned over flexible strap post portions that may be monolithic extensions of the respective upper and lower elongate extensions. For some embodiments, the split sleeve may include a rigid plastic material such as PVC, Nylon®, ABS plastic, or the like or high strength metals or alloys such as steel, aluminum or the like.

The goggle assembly embodiments 22, 22A shown and discussed herein may include a lens 104 which has an outer perimeter edge which may be shaped to match a shape of the lens aperture 29 of the goggle frame 24 and which may be releasably secured to the lens receptacle 28 of the anterior portion 26 of the goggle frame 24. The lens 104 may be made from a thin, flexible and clear polymer material with suitable optical properties and with sufficient strength and resilience to provide protection to a wearer's eyes. For some embodiments, the lens 104 may be made from a high strength polymer such as polycarbonate and may have a thickness of about 0.02 inches to about 0.05 inches, more specifically, about 0.03 inches to about 0.04 inches. Some such lens embodiments may be formed by molding or cutting from a sheet of material by methods such as die cutting, laser cutting or the like. The lens 104 may also include one or more of any desired optical coating such as an anti-fog coating, anti-reflective coating, polarized coating, shading coating or the like. Some lens embodiments 104 may also include a pair of tear off posts 106 disposed on and extending outwardly from opposite lateral sides of the lens 104 as shown in FIG. 7. For some embodiments, a third tear off post 108 may be disposed on and extend outwardly from a tear off post support 110 that may include a web of polymer material secured between respective strap end portions 38, 44 of the elongate upper extension 32 and elongate lower extension 40 shown in FIG. 7. In some instances, the third tear off post 108 may be disposed on a post support (not shown) which may be disposed on and secured to the elastic strap 98 adjacent the left side of the goggle assembly 22. Such an elastic strap 98, as may be commonly found on currently available sport goggles, may have a first end 112 secured to the left strap post 46 and a second end 114 secured to the right strap post 64. The elastic strap 98 may be secured to the strap posts 46, 64 of the goggle assembly 22 and may also include a length adjustment buckle (not shown) to allow for a customized fit of the elastic strap 98 and goggle assembly 22 to a wearer's face.

Figure 5:
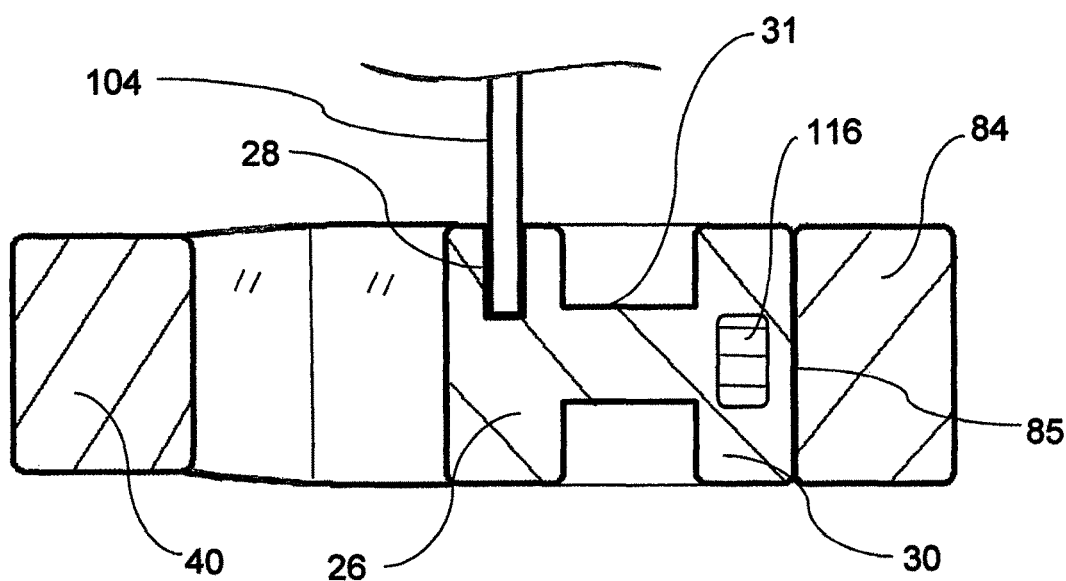
FIG. 5 is a cross section taken along lines 5-5 of FIG. 4.
Figure 6:
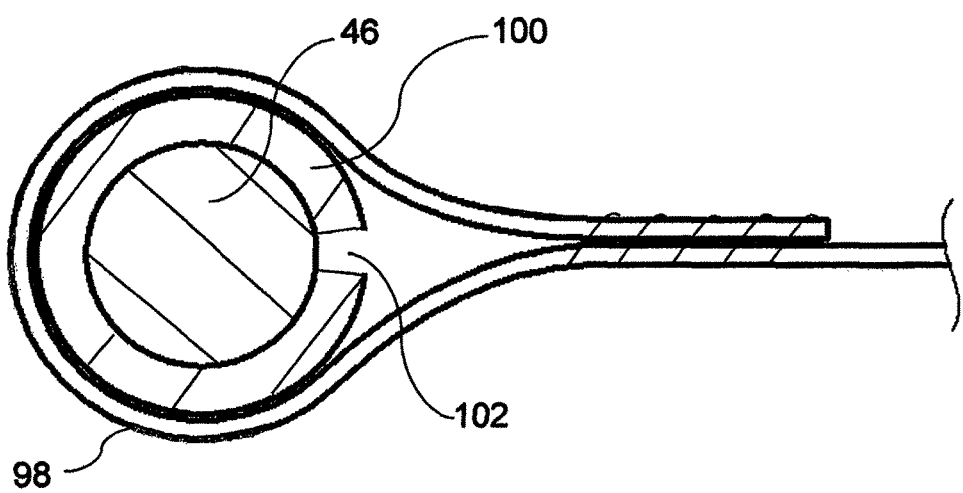
FIG. 6 is a cross section taken along lines 6-6 of FIG. 4.

For some embodiments, the goggle frame 24 may include a resilient reinforcement wire 116 extending along an outer perimeter of the goggle frame 24 as shown in FIG. 5 and by the dashed lines in FIGS. 3 and 9. The resilient reinforcement wire 116 may have a shape that is configured to conform the outer ends of the posterior frame portion 30 to a wearer's face. This may be particularly useful for embodiments wherein a separation of the outer ends of the posterior frame portion 30 and anterior frame portion 26 decreases towards the outer ends 70, 72 of the goggle frame 24 as shown in FIG. 3. The resilient reinforcement wire 116 may have a relaxed shape wherein no external forces are being applied to the resilient reinforcement wire 116. In some cases, the relaxed shape may have a separation between outer ends that is less than a separation of the outer ends when the respective goggle assembly embodiment 22 that includes the resilient reinforcement wire 116 is placed on a wearer's face. For such embodiments, the resilient reinforcement wire 116 may provide an elastic restorative inward force that effectively pushes the outer ends of the goggle frame inwardly to better seat the outer ends of the goggle frame 24 against the sides or temples of a wearer's face. In some cases, the resilient reinforcement wire 116 may be disposed and embedded within material of the posterior frame portion 30 of the goggle frame 24. For some embodiments, the resilient reinforcement wire 116 may include a high strength elastic resilient a material such as spring steel, Elgiloy®, and nickel titanium alloy. In some instances, the resilient reinforcement wire 116 may have an outer diameter of about 0.02 inches to about 0.06 inches.

For some embodiments, the respective goggle ends of the extensions 32, 40, 52 and 58 are secured to and extend from respective positions on the anterior frame portion 26 that are about one half to about three quarters of the distance from the centerline 78 to the respective outer ends 70, 72. For some embodiments, the extensions 32, 40, 52 and 58 extend from the respective positions on the anterior frame portion 26 at an angle between a longitudinal axis 122 of each of the extensions and a tangent line 124 with respect to the anterior frame portion 26 that extends away from the anterior frame portion 26 as indicated by arrow 120 shown in FIG. 11. In some instances, the angle indicated by arrow 120 may be about 30 degrees to about 50 degrees, more specifically, about 35 degrees to about 45 degrees.

With regard to the above detailed description, like reference numerals used therein may refer to like elements that may have the same or similar dimensions, materials and configurations. While particular forms of embodiments have been illustrated and described, it will be apparent that various modifications can be made without departing from the spirit and scope of the embodiments discussed. Accordingly, it is not intended that the invention be limited by the forgoing detailed description.

The entirety of each patent, patent application, publication and document referenced herein is hereby incorporated by reference. Citation of the above patents, patent applications, publications and documents is not an admission that any of the foregoing is pertinent prior art, nor does it constitute any admission as to the contents or date of these documents.

Modifications may be made to the foregoing embodiments without departing from the basic aspects of the technology. Although the technology may have been described in substantial detail with reference to one or more specific embodiments, changes may be made to the embodiments specifically disclosed in this application, yet these modifications and improvements are within the scope and spirit of the technology. The technology illustratively described herein suitably may be practiced in the absence of any element(s) not specifically disclosed herein. Thus, for example, in each instance herein any of the terms "comprising," "consisting essentially of," and "consisting of" may be replaced with either of the other two terms. The terms and expressions which have been employed are used as terms of description and not of limitation, and use of such terms and expressions do not exclude any equivalents of the features shown and described or portions thereof, and various modifications are possible within the scope of the technology claimed. The term "a" or "an" may refer to one of or a plurality of the elements it modifies (e.g., "a reagent" can mean one or more reagents) unless it is contextually clear either one of the elements or more than one of the elements is described. Although the present technology has been specifically disclosed by representative embodiments and optional features, modification and variation of the concepts herein disclosed may be made, and such modifications and variations may be considered within the scope of this technology.

Certain embodiments of the technology are set forth in the claim(s) that follow(s).

What is claimed is:

1. A goggle assembly, comprising:
    a goggle frame including an anterior frame portion with a lens receptacle disposed about an interior perimeter that defines a lens aperture and a posterior frame portion which is disposed adjacent and secured to the anterior frame portion and which is configured to fit to an outside surface of a wearer's face around the wearer's eyes;
    an elongate left upper extension including a goggle end secured to an upper portion of the anterior frame portion at a position which is about one half to about three quarters of a distance from a centerline of the goggle assembly to a respective outer end of the goggle frame, a strap end that is disposed opposite the goggle end, a tapered structure that tapers to a smaller transverse cross section from the goggle end to the strap end and a length of about 6 inches to about 10 inches from the strap end to the centerline of the goggle assembly which is sufficient to allow the strap end of the elongate left upper extension to wrap behind a left side of the entire goggle frame;
    an elongate left lower extension including a goggle end secured to a lower portion of the anterior frame portion at a position which is about one half to about three quarters of a distance from the centerline of the goggle assembly to the respective outer end of the goggle frame, a strap end that is disposed opposite the goggle end, a tapered structure that tapers to a smaller transverse cross section from the goggle end to the strap end and a length of about 6 inches to about 10 inches from the strap end to the centerline of the goggle assembly which is sufficient to allow the strap end of the elongate left lower extension to wrap behind the left side of the entire goggle frame;
    a left strap post having an upper end secured to the strap end of the elongate left upper extension and a lower end secured to the strap end of the elongate left lower extension;
    an elongate right upper extension including a goggle end secured to an upper portion of the anterior frame portion at a position which is about one half to about three quarters of a distance from the centerline of the goggle assembly to a respective outer end of the goggle frame, a strap end that is disposed opposite the goggle end, a tapered structure that tapers to a smaller transverse cross section from the goggle end to the strap end and a length of about 6 inches to about 10 inches from the strap end to the centerline of the goggle assembly which is sufficient to allow the strap end of the elongate right upper extension to wrap behind a right side of the entire goggle frame;
    an elongate right lower extension including a goggle end secured to a lower portion of the anterior frame portion at a position which is about one half to about three quarters of a distance from the centerline of the goggle assembly to the respective outer end of the goggle frame, a strap end that is disposed opposite the goggle end, a tapered structure that tapers to a smaller transverse cross section from the goggle end to the strap end and a length of about 6 inches to about 10 inches from the strap end to the centerline of the goggle assembly which is sufficient to allow the strap end of the elongate right lower extension to wrap behind the right side of the entire goggle frame;
    a right strap post having an upper end secured to the strap end of the elongate right upper extension and a lower end secured to the strap end of the elongate right lower extension; and
    wherein the tapered structure of the elongate extensions includes an inclusive taper angle of about 0.5 degrees to about 2 degrees.

2. The goggle assembly of claim 1 wherein a separation between the anterior frame portion and posterior frame portion tapers to a reduced relative separation towards outer ends of the goggle frame.

3. The goggle assembly of claim 2 wherein the anterior frame portion and posterior frame portion taper to a reduced relative separation towards the outer ends of the goggle frame and merge together at the outer ends of the goggle frame.

4. The goggle assembly of claim 1 wherein the length of each strap post and length of the respective elongate extensions secured thereto are configured such that each strap post is disposed substantially vertically and the upper extension extends along a respective upper portion of the anterior frame portion and the lower extension extends along a respective lower portion of the anterior frame portion in order to minimize impact of the extensions on the wearer's field of view and provide a band of unobstructed vision having a vertical width of at least about 1 inch.

5. The goggle assembly of claim 1 wherein each of the elongate extensions comprises a flexible resilient structure configured to retain its shape in a relaxed unconstrained state but with sufficient flexibility to wrap around a wearer's head and a helmet cut out.

6. The goggle assembly of claim 1 further comprising a lens including an outer perimeter edge which is releasably secured to the goggle frame.

7. The goggle assembly of claim 1 further comprising an elastic strap having a first end secured to the left strap post and a second end secured to the right strap post.

8. The goggle assembly of claim 1 wherein the goggle frame comprises a flexible polymer.

9. The goggle assembly of claim 8 wherein the flexible polymer of the goggle frame comprises polyurethane.

10. The goggle assembly of claim 1 further comprising an elastic compressible foam gasket disposed on and secured to a face surface the posterior frame portion.

11. The goggle assembly of claim 1 wherein the elongate extensions are molded as monolithic structures which are continuous extensions of the anterior frame portion of the goggle frame.

12. The goggle assembly of claim 1 wherein the elongate extensions are separate structures with respect to the goggle frame and which are secured to the anterior frame portion of the goggle frame.

13. The goggle assembly of claim 1 wherein a left side portion of the goggle frame and a right side portion of the goggle frame are shaped so as to provide a lateral peripheral angle of vision that extends to at least about 125 degrees from a lateral axis of symmetry line of a wearer's head.

14. The goggle assembly of claim 1 wherein the frame further comprises a nose cut out disposed at the center of the lower portion of the anterior frame portion and a lower portion of the posterior frame portion.

15. The goggle assembly of claim 1 wherein the right and left strap posts each comprise a tubular rigid outer sleeve that extends from respective upper and lower ends of each strap post.

16. The goggle assembly of claim 15 wherein each rigid outer sleeve comprises a split sleeve with an elongate tubular structure with a narrow longitudinal gap in a wall of the tubular structure extending an entire longitudinal length of the rigid outer sleeve.

17. A goggle assembly, comprising:
a goggle frame including an anterior frame portion with a lens receptacle disposed about an interior perimeter that defines a lens aperture and a posterior frame portion which is disposed adjacent and secured to the anterior frame portion and which is configured to fit to an outside surface of a wearer's face around the wearer's eyes;
an elongate left upper extension including a goggle end secured to an upper portion of the anterior frame portion, a strap end that is disposed opposite the goggle end, a tapered structure that tapers to a smaller transverse cross section from the goggle end to the strap end and a length of about 6 inches to about 10 inches from the strap end to a centerline of the goggle assembly which is sufficient to allow the strap end of the elongate left upper extension to wrap behind a left side of the entire goggle frame such that the strap end of the elongate left upper extension is disposed completely outside the wearer's left side field of peripheral vision;
an elongate left lower extension including a goggle end secured to a lower portion of the anterior frame portion, a strap end that is disposed opposite the goggle end, a tapered structure that tapers to a smaller transverse cross section from the goggle end to the strap end and a length of about 6 inches to about 10 inches from the strap end to the centerline of the goggle assembly which is sufficient to allow the strap end of the elongate left lower extension to wrap behind the left side of the entire goggle frame such that the strap end of the elongate left lower extension is disposed completely outside the wearer's left side field of peripheral vision;
a left strap post having an upper end secured to the strap end of the elongate left upper extension and a lower end secured to the strap end of the elongate left lower extension;
an elongate right upper extension including a goggle end secured to an upper portion of the anterior frame portion, a strap end that is disposed opposite the goggle end, a tapered structure that tapers to a smaller transverse cross section from the goggle end to the strap end and a length of about 6 inches to about 10 inches from the strap end to the centerline of the goggle assembly which is sufficient to allow the strap end of the elongate right upper extension to wrap behind a right side of the entire goggle frame such that the strap end of the elongate right upper extension is disposed completely outside the wearer's right side field of peripheral vision;
an elongate right lower extension including a goggle end secured to a lower portion of the anterior frame portion, a strap end that is disposed opposite the goggle end, a tapered structure that tapers to a smaller transverse cross section from the goggle end to the strap end and a length of about 6 inches to about 10 inches from the strap end to the centerline of the goggle assembly which is sufficient to allow the strap end of the elongate right lower extension to wrap behind the right side of the entire goggle frame such that the strap end of the elongate right lower extension is disposed completely outside the wearer's right side field of peripheral vision;
a right strap post having an upper end secured to the strap end of the elongate right upper extension and a lower end secured to the strap end of the elongate right lower extension; and
wherein the tapered structure of the elongate extensions includes an inclusive taper angle of about 0.5 degrees to about 2 degrees.

18. The goggle assembly of claim 17 further comprising:
a gap comprising a rearward spatial separation between a left edge of a lens aperture of the goggle frame and a front edge of the left strap post of about 0.5 inches to about 3 inches; and
a gap comprising a rearward spatial separation between a right edge of the lens aperture of the goggle frame and a front edge of the right strap post of about 0.5 inches to about 3 inches.

19. The goggle assembly of claim 1 further comprising:
a gap comprising a rearward spatial separation between a left edge of a lens aperture of the goggle frame and a front edge of the left strap post of about 0.5 inches to about 3 inches; and
a gap comprising a rearward spatial separation between a right edge of the lens aperture of the goggle frame and a front edge of the right strap post of about 0.5 inches to about 3 inches.

* * * * *